US012745952B2

(12) United States Patent
Guido-Sanz et al.

(10) Patent No.: US 12,745,952 B2
(45) Date of Patent: Sep. 29, 2026

(54) SYSTEM TO VISUALIZE, MEASURE, AND TRACK SKIN ABNORMALITIES

(71) Applicants: University of Central Florida Research Foundation, Inc., Orlando, FL (US); New Jersey Institute of Technology, Newark, NJ (US)

(72) Inventors: Francisco Guido-Sanz, Orlando, FL (US); Mindi Anderson, Orlando, FL (US); Desiree Diaz, Orlando, FL (US); Steven Talbert, Orlando, FL (US); Salam Daher, Newark, NJ (US); Dahlia Musa, Newark, NJ (US)

(73) Assignees: University of Central Florida Research Foundation, Inc., Orlando, FL (US); New Jersey Institute of Technology, Newark, NJ (US)

( * ) Notice: Subject to any disclaimer, the term of this patent is extended or adjusted under 35 U.S.C. 154(b) by 66 days.

(21) Appl. No.: 18/936,184

(22) Filed: Nov. 4, 2024

(65) Prior Publication Data

US 2025/0057470 A1 Feb. 20, 2025

Related U.S. Application Data

(63) Continuation of application No. PCT/US2023/024447, filed on Jun. 5, 2023.

(Continued)

(51) Int. Cl.

*A61B 5/00* (2006.01)
*G16H 10/60* (2018.01)

(Continued)

(52) U.S. Cl.

CPC ............ *A61B 5/445* (2013.01); *A61B 5/0064* (2013.01); *A61B 5/0073* (2013.01); *A61B 5/444* (2013.01);

(Continued)

(58) Field of Classification Search

None

See application file for complete search history.

(56) References Cited

U.S. PATENT DOCUMENTS

2015/0025342 A1* 1/2015 Papazoglou ....... A61B 5/14546 600/322
2019/0200917 A1 7/2019 Murphy et al.

(Continued)

OTHER PUBLICATIONS

Fellipe M. C. Barbosa et al. "Accurate Chronic Wound Area Measurement using Structure from Motion" 2020 pp. 208-213. 33rd International Symposium on Computer-Based Medical Systems. Natal, Brazil.

(Continued)

*Primary Examiner* — Yi-Shan Yang
(74) *Attorney, Agent, or Firm* — Anton J. Hopen; Trenam Law

(57) ABSTRACT

A method of skin anomaly assessment, measurement, and monitoring is disclosed. The three-dimensional topology of a skin anomaly is digitally scanned, and a three-dimensional model of the skin anomaly is computationally constructed. From the three-dimensional model, length, width, depth, perimeter, and surface area measurements of the skin anomaly are derived. This information may be quantified by volume surface area, and/or distance along the surface of the anomaly, and measured against models of anticipated healing for medical monitoring and training.

15 Claims, 3 Drawing Sheets

Related U.S. Application Data

(60) Provisional application No. 63/348,691, filed on Jun. 3, 2022.

(51) Int. Cl.
*G16H 50/50* (2018.01)
*G16H 80/00* (2018.01)

(52) U.S. Cl.
CPC ........... *A61B 5/7425* (2013.01); *G16H 10/60* (2018.01); *G16H 50/50* (2018.01); *G16H 80/00* (2018.01)

(56) References Cited

U.S. PATENT DOCUMENTS

| | | | | |
|---|---|---|---|---|
| 2021/0104043 | A1* | 4/2021 | Crawford | G06T 7/0014 |
| 2021/0251503 | A1* | 8/2021 | Gurevich | A61B 5/7267 |
| 2021/0290152 | A1 | 9/2021 | Vogel | |
| 2021/0330245 | A1 | 10/2021 | Dobak, III et al. | |
| 2022/0122734 | A1* | 4/2022 | Ferrante | G06N 3/084 |
| 2022/0328189 | A1 | 10/2022 | Zhou et al. | |

OTHER PUBLICATIONS

Filipe Ferreira et al. “Approach for the Wound Area Measurement with Mobile Devices” 2021 pp. 1-4.New Jersey.

International Search Report and Written Opinion issued Sep. 1, 2023 for corresponding PCT Application No. PCT/US 23/24447 with an International Filing Date of Jun. 5, 2023.

Line Bisgaard Jørgensen et al. “Monitoring Wound Healing of Diabetic Foot Ulcers Using Two-Dimensional and Three-Dimensional Wound Measurement Techniques: A Prospective Cohort Study” 2020. pp. 553-563. vol. 9, No. 10. Wound Healing Society. Copenhagen, Denmark.

Chunhui Liu et al. “Wound area measurement with 3D transformation and smartphone images” 2019 pp. 1-21. BMC Bioinformatics. Beijing, China.

Houman Mirzaalian Dastjerdi et al. “Measuring Surface Area of Skin Lesions with 2D and 3D Algorithms” 2019. pp. 1-9. Article ID 4035148. International Journal of Biomedical Imaging. Erlangen, Germany.

International Preliminary Report on Patentability issued Dec. 12, 2024 for corresponding PCT Application No. PCT/US 23/24447 with an International Filing Date of Jun. 5, 2023.

David Sanchez-Jimenez et al. “SfM-3DULC: Reliability of a new 3D wound measurement procedure and its accuracy in projected area” Journal 2021 pp. 44-51. Wiley. Valencia, Spain.

Kriangkrai Tassanavipas et al. “An Integrated Hardware and Software Application to Support Wound Measurement Using a 3D Scanner and Image Processing Techniques” 2020, pp. 55-73. The Open Biomedical Engineering Journal. Bangkok, Thailand.

* cited by examiner

| | | Physical | | Image | | Software | | | Conover post hoc | | |
|---|---|---|---|---|---|---|---|---|---|---|---|
| | Wound | Mean ± SE | SD | Mean ± SE | SD | Mean ± SE | SD | Friedman | P vs I | P vs S | I vs S |
| Length | 1 | 51.10 ± 1.11 | 4.73 | 52.39 ± 0.74 | 3.16 | 53.49 ± 0.88 | 3.75 | **0.042** | 0.143 | **0.017** | 0.324 |
| | 2 | 71.52 ± 1.02 | 4.31 | 77.70 ± 0.54 | 2.29 | 73.83 ± 0.36 | 1.54 | **< .001** | **< .001** | 0.251 | **< .001** |
| | 3 | 94.36 ± 1.49 | 6.30 | 100.60 ± 1.20 | 5.08 | 97.29 ± 1.02 | 4.35 | **< .001** | **< .001** | 0.054 | 0.054 |
| | 4 | 60.89 ± 0.84 | 3.57 | 68.55 ± 0.74 | 3.14 | 60.57 ± 0.49 | 2.07 | **< .001** | **< .001** | 0.741 | **< .001** |
| Width | 1 | 46.35 ± 0.92 | 3.91 | 49.23 ± 0.84 | 3.55 | 48.67 ± 0.79 | 3.35 | **0.002** | **0.002** | **0.020** | **0.362** |
| | 2 | 67.48 ± 0.96 | 4.05 | 74.45 ± 0.90 | 3.82 | 69.72 ± 0.31 | 1.30 | **< .001** | **< .001** | 0.105 | **0.003** |
| | 3 | 63.60 ± 1.22 | 5.18 | 69.88 ± 0.73 | 3.09 | 64.55 ± 2.68 | 11.39 | **< .001** | **< .001** | **0.012** | **0.012** |
| | 4 | 57.39 ± 1.13 | 4.78 | 65.24 ± 0.75 | 3.18 | 58.17 ± 0.72 | 3.04 | **< .001** | **< .001** | 0.620 | **< .001** |
| Depth | 1 | 13.54 ± 1.00 | 4.26 | 13.94 ± 0.96 | 4.09 | 13.73 ± 1.18 | 4.99 | 0.211 | 0.191 | 0.741 | 0.105 |
| | 2 | 20.13 ± 1.77 | 7.50 | 20.12 ± 2.05 | 8.71 | 17.90 ± 1.96 | 8.31 | 0.115 | 0.620 | 0.054 | 0.143 |
| | 3 | 30.06 ± 1.54 | 6.52 | 20.96 ± 0.74 | 3.15 | 32.09 ± 2.48 | 10.54 | **< .001** | **< .001** | 0.410 | **< .001** |
| | 4 | 25.82 ± 1.66 | 7.05 | 20.36 ± 0.72 | 3.04 | 21.09 ± 0.98 | 4.18 | **0.006** | **0.012** | **0.008** | 0.869 |
| Perimeter | 1 | 152.95 ± 13.61 | 57.76 | 162.18 ± 8.61 | 36.54 | 160.25 ± 0.75 | 3.18 | 0.078 | **0.036** | 0.120 | 0.561 |
| | 2 | 203.11 ± 11.26 | 47.77 | 226.73 ± 12.13 | 51.46 | 229.48 ± 2.51 | 10.67 | **< .001** | **< .001** | **0.017** | 0.143 |
| | 3 | 238.35 ± 15.30 | 64.90 | 258.03 ± 15.73 | 66.74 | 257.81 ± 2.37 | 10.06 | **0.042** | **0.017** | 0.143 | 0.324 |
| | 4 | 188.81 ± 9.32 | 39.54 | 208.77 ± 12.43 | 52.72 | 198.76 ± 1.52 | 6.47 | **0.003** | **0.002** | 0.251 | **0.037** |
| Surface Area | 1 | 2389.23 ± 532.35 | 2258.59 | 2102.95 ± 153.99 | 653.34 | 2163.67 ± 25.90 | 109.88 | 0.066 | 0.076 | **0.037** | 0.741 |
| | 2 | 3593.45 ± 262.23 | 1112.55 | 4493.91 ± 471.90 | 2002.10 | 4892.76 ± 24.29 | 103.06 | **< .001** | **0.017** | **< .001** | 0.143 |
| | 3 | 5950.36 ± 905.50 | 3841.71 | 5904.89 ± 635.13 | 2694.64 | 7986.66 ± 52.67 | 223.44 | **< .001** | 0.191 | **< .001** | **0.008** |
| | 4 | 3349.20 ± 413.07 | 1752.49 | 4250.97 ± 452.97 | 1921.78 | 6219.16 ± 108.94 | 462.17 | **< .001** | **0.017** | **< .001** | **0.030** |

Table 2: Results of the Friedman and Conover tests evaluating variability between physical (P), 2D image (I), and 3D scan (S) measurement techniques. Descriptive data include mean, standard error (SE), and standard deviation (SD). Units for length, width, depth, and perimeter are in mm, and units for surface area are in mm2. Statistically significant p-values ($p < 0.05$) are in bold.

Fig. 2

SYSTEM TO VISUALIZE, MEASURE, AND TRACK SKIN ABNORMALITIES

CROSS-REFERENCE TO RELATED APPLICATIONS

This nonprovisional application is a continuation of, and claims priority to, PCT International Application No. PCT/US2023/024447, entitled "SYSTEM TO VISUALIZE, MEASURE AND TRACK SKIN ABNORMALITIES," filed on Jun. 5, 2023, by the same inventors, which claims priority to provisional Application No. 63/348,691, entitled "System to visualize, measure and track skin abnormalities," filed on Jun. 3, 2022, by the same inventors, the entirety of which are incorporated herein by reference.

BACKGROUND OF THE INVENTION

1. Field of the Invention

This invention relates, generally, to skin abnormality measurements. More specifically, it relates to an improved system and method to measure and track skin abnormality (such as a wound site) characteristics using automatically generated three dimensional (3D) representations of skin abnormalities.

2. Technology Background

In order to accurately and effectively assess and/or treat a wound on a patient, a healthcare provider must gain an understanding of wound measurements and characteristics, including repeated measurements performed over time to evaluate and track wound healing metrics. A standard method to measure wounds, such as pressure injuries, is to consider the direct measurements between two points representing the length (L) and the width (W) of the wound and then calculate its area by L×W. For example, to measure the volume of a wound, a cotton swab (or similar elongated device, typically including a sterile cloth component at a patient interface portion of the device) is placed in the deepest part of the wound to gauge its depth (D). A wound volume is subsequently calculated using purely linear dimensional measurements, namely the length, width, and depth of the visible wound site.

As such, current methods of assessing wounds are limited to mapping wound topographies through such linear measurements without considering the entire surface area, topography, or geometry of a wound site, including the perimeter or undermining of the wound. Such methods often result in inaccurate measurements since wounds do not typically have purely linear dimensions. Additionally, these area and volume equations are intended to measure square, rectangular, and similar substantially uniform and/or parametric shapes; as such, when measuring wounds, simply area and volume calculations using linear dimensions may result in overestimations or underestimations and fail to provide an accurate overview of the wound site as a whole. Moreover, different healthcare providers may judge the greatest length, width, and depth dimensions differently (such as by selecting different start points and end points from which dimensions are calculated), further causing variability in wound measurements.

In addition, in order to provide effective care to a patient, a healthcare provider must be aware of intricate details of conditions, including accurate details regarding skin abnormality characteristics. Simplistic area and volume calculations, based on inaccurate measurements, fail to provide a healthcare provider with sufficient detailed information to determine an effective case management and healing plan. Moreover, the insertion of a cotton swab or other device into a wound of a patient not only may fail to provide accurate dimensional characteristics for the wound site, but also cause discomfort for the patient and risk infection or irritation of the wound site.

Attempts have been made to provide two-dimensional (2D) images of a skin abnormality to provide a non-contact method of measuring the skin abnormality, such as a wound site. However, such two-dimensional images attempt to project a three-dimensional object or location of interest; as such, measurements are typically inaccurate, such as due to occlusion, image angles, warping, curvature, and other three-dimensional characteristics that do not translate to a two-dimensional image. Moreover, a two-dimensional image of a skin abnormality fails to provide data relating to a depth or a height of the skin abnormality; as such, contact must occur through a patient-interactive (and potentially invasive) measurement regardless of the use of a two-dimensional image.

Chronic wounds fail to progress in an orderly and timely process to restore skin integrity, thereby requiring additional monitoring. Such chronic, non-healing, or poorly-healing skin abnormalities affect millions of wound patients annually, with costs associated with monitoring and treating such abnormalities ranging into the billions of dollars each year. Moreover, wounds that fail to timely heal under a regular management plan may negatively impact a patient's quality of life throughout the duration of the wound.

Accordingly, what is needed is an improved system and method of tracking skin abnormalities, such as a wound site, by automatically scanning and analyzing a three-dimensional topology of a skin anomaly without being limited to linear dimension measurements. However, in view of the art considered as a whole at the time the present invention was made, it was not obvious to those of ordinary skill in the field of this invention as to how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a system and method of automatically and accurately tracking skin abnormalities across three dimensions is now met by a new, useful, and nonobvious invention.

The present invention includes a method of skin anomaly measurement and monitoring. The method includes the step of receiving, at a computing device, a scan of a three-dimensional topology of a skin anomaly. The scan of the three-dimensional topology of the skin anomaly is converted, via the computing device, into a three-dimensional model of the skin anomaly. The three-dimensional model has characteristics and dimensions matching the three-dimensional topology. The method includes the step of displaying, via a display device in communication with the computing device, the three-dimensional model. The method includes the step of receiving, on the three-dimensional model and via the computing device, an input of at least a start point and an end point. The start point and the end point are associated with at least one dimension of the three-dimensional model of the skin anomaly.

Based on the input of at least the start point and the end point, the method includes a step of automatically calculating a dimension of the skin anomaly, with the dimension being selected from the group consisting of a length, a width, a depth, a perimeter, a surface area, and a volume. In an embodiment, the method includes the step of automatically calculating, based on a plurality of inputs received on the three-dimensional model and via the computing device, each of the length, the width, the depth, the perimeter, and the surface area of the skin anomaly.

In some embodiments, the scan of the three-dimensional topology of the skin anomaly is a first scan, and the method includes the step of receiving, at the computing device, a second scan of the three-dimensional topology of the skin anomaly, with the second scan being taken subsequent to the first scan.

In an embodiment, the three-dimensional model of the skin anomaly is a first three-dimensional model of the skin anomaly, and the method includes the step of converting, via the computing device, the second scan of the three-dimensional topology of the skin anomaly into a second three-dimensional model of the skin anomaly. In some embodiments, differences in dimensions between the first three-dimensional model and the second three-dimensional model are tracked via the computing device. In an embodiment, the computing device generates, based on the differences in dimensions between the first three-dimensional model and the second three-dimensional model, a simulated healing model for the skin anomaly. In embodiments, the simulated healing model is based on the surface area and the perimeter of each of the first three-dimensional model and the second three-dimensional model. In some embodiments, the differences in dimensions between the first three-dimensional model and the second three-dimensional model is selected from the group consisting of the surface area, the perimeter, the length measured along a surface of the skin anomaly, the width measured along the surface of the skin anomaly, and the depth measured along the surface of the skin anomaly.

In an embodiment, the method includes the step of pretraining, from a database of skin anomaly healing progression images, a machine learning model on the computing device. In some embodiments, a simulated healing model for the skin anomaly is generated via the computing device and based on the machine learning model. In embodiments, the simulated healing model is based on the surface area and the perimeter of the three-dimensional model. In some embodiments, simulated healing model is based on the differences in dimensions that are selected from the group consisting of the surface area, the perimeter, the length measured along a surface of the skin anomaly, the width measured along the surface of the skin anomaly, and the depth measured along the surface of the skin anomaly.

In some embodiments, the three-dimensional model of the skin anomaly is a first three-dimensional model of the skin anomaly, and the method includes the step of converting, via the computing device, the second scan of the three-dimensional topology of the skin anomaly into a second three-dimensional model of the skin anomaly. In an embodiment, the method includes the step of comparing the second three-dimensional model of the skin anomaly to the simulated healing model for the skin anomaly. Based on a determination that each of the surface area and the perimeter of the second three-dimensional model of the skin anomaly is greater than a surface area and a perimeter of the simulated healing model for the skin anomaly, the method includes the step of generating, via the computing device, an alert.

In some embodiments, the display device includes a digital overlay component selected from the group consisting of virtual reality, augmented reality, and mixed reality. In an embodiment, the step of displaying the three-dimensional model includes displaying, via a plurality of display devices that are remote to each other, the three-dimensional model at different locations, such that the three-dimensional model is simultaneously interactable to a plurality of different users via the digital overlay component.

In an embodiment, the three-dimensional model and the automatically calculated dimension of the skin anomaly are integrated into an electronic health record of a subject associated with the skin anomaly.

In an embodiment, the method includes the step of establishing a spatial anchor for the three-dimensional model, wherein the computing device is configured to receive one or more additional measurements from the spatial anchor.

An object of the invention is to improve upon skin abnormality and anomaly (such as wound site) detection and tracking systems and methods by automatically measuring wound characteristics across three dimensions, including an outer surface area and perimeter and a volume, without being limited to purely linear and direct (or shortest distance) measurements.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2 depicts a table of the results of Friedman and Conover tests evaluating variability between physical, 2D image, and 3D scan measurement techniques for a set of wounds, including measurements of wound length, width, depth, perimeter, and surface area.

DETAILED DESCRIPTION OF THE PREFERRED EMBODIMENT

Figure 1B:
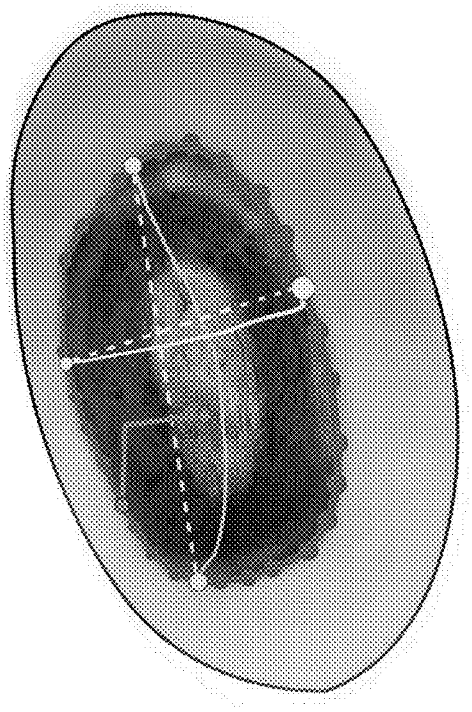
FIG. 1B depicts a 3D model of a skin anomaly, showing a plurality of measurements, in accordance with an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise. All numerical designations, including ranges, are approximations which are varied up or down by increments of 1.0 or 0.1, as appropriate. It is to be understood, even if it is not always explicitly stated that all numerical designations are preceded by the term "about." As used herein, "about," "approximately," or "substantially" refer to being within an acceptable error range for the particular value as determined by one of ordinary skill in the art, which will depend in part on how the value is measured or determined. As used herein, the terms "about," "approximately," and "substantially" refer to ±10% of the numerical; it should be understood that a numerical including an associated range with a lower boundary of greater than zero must be a non-zero numerical, and the terms "about," "approximately," and "substantially" should be understood to include only non-zero values in such scenarios.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, "target area" is used to describe a skin abnormality, such as a pressure injury, a dermatological condition (such as a melanoma, a blister, a lesion, skin cancer, and similar conditions), a burn wound, an ulcer (such as a diabetic foot ulcer, a vascular ulcer, and similar ulcers), a penetrating wound (such as a puncture, a gunshot, a stab wound, and similar penetrations), a non-penetrating wound (such as an abrasion, contusion, laceration, and similar wounds that have not broken the skin at the time of evaluation), a non-surface wound (such as a subcutaneous or subdural wound, including an abscess, necrotizing fasciitis, tunneling, undermining, and similar non-surface wounds), and other wounds.

As used herein, "subject" is used to describe a human, other animal, or an object having a target area for whom or for which assessment, evaluation, monitoring, and/or tracking of the target area is desired.

As used herein, "computing device" is used to describe an electronic device that is capable of storing and processing data and includes a personal computer, cellular device, tablet, console, server, media device, and similar devices.

The present invention includes an improved system and method of assessing, evaluating, monitoring, and tracking a target area of a subject. The system and method include a three-dimensional (3D) scanning and display technique to analyze, in three dimensions, characteristics of the target area using a model of the target area including accurate topographies, lengths, widths, depths, perimeters, surface areas, and volumes. The system and method automatically measure target area characteristics across three dimensions without being restricted to linear measurements, thereby improving upon the accuracy of such measurements and subsequent target area tracking. Embodiments of the present invention can be implemented not only in clinical settings involving subjects seeking or otherwise receiving the advice of a health care provider, but also in training settings for health care providers. Embodiments of the system and method will be described in greater detail in the sections herein below.

In an embodiment, a computing device receives, as an input, one or more three-dimensional scans of a target area, and the computing device subsequently displays the one or more three-dimensional scans on a display device associated therewith (such as wirelessly or through a wired connection). The computing device can receive the input 3D digital scan(s) from any other computing device or electronic device that is capable of transmitting data to the computing device. As such, the computing device, after receiving the input one or more three-dimensional scans, displays a model of the target area on the display device. In an embodiment, the computing device automatically aligns the model using an optimization process (such as an iterative closest point model) to align the mesh via translation, rotation, and scale. After receiving and displaying at least one of the one or more three-dimensional scans, the computing device receives an input from a device user or from an automated process executed on the computer device on the model of the target area, with the input being used by the computing device to automatically execute one or more measurements.

Figure 1A:
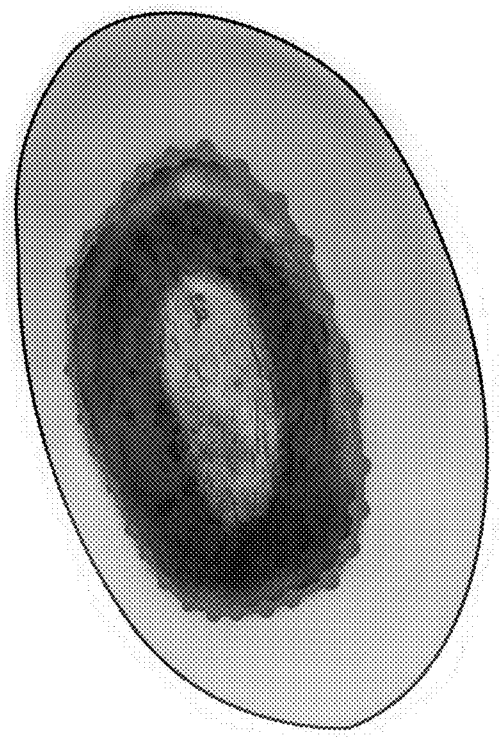
FIG. 1A depicts a 3D model of a skin anomaly, showing a perimeter measurement, in accordance with an embodiment of the present invention.
Figure 1D:
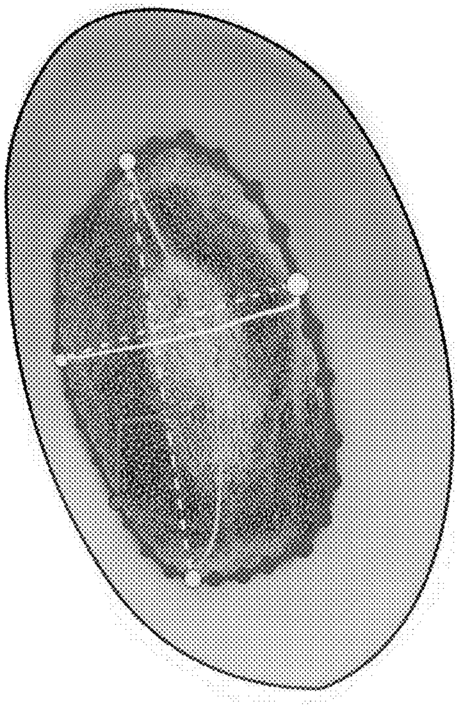
FIG. 1D depicts a 3D model of a skin anomaly, showing a plurality of measurements, in accordance with an embodiment of the present invention.
Figure 1C:
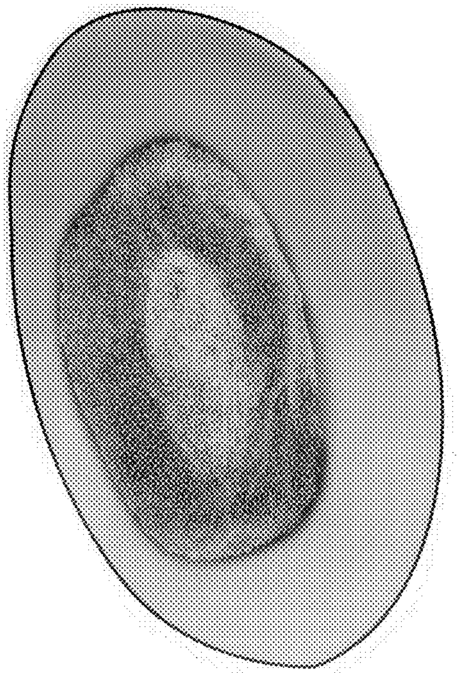
FIG. 1C depicts a 3D model of a skin anomaly, showing a surface area measurement, in accordance with an embodiment of the present invention.

Specifically, in an embodiment (as shown in FIGS. 1A-1D), the computing device automatically calculates one or more linear measurements representing a length, a width, or a depth of a target area after receiving at least two inputs from a device user or from an automated process executed on the computer device on the model of the target area. For example, in an embodiment, the computing device calculates the length of a target area as a Euclidean distance between a start point and an end point as received by the computer device based on at least two inputs from a device user or from an automated process executed on the computer device on the model of the target area. Similarly, the width and the depth of the target area can be automatically calculated by the computing device as a Euclidean distance between a starting point and an end point based on at least two inputs from a device user or from an automated process executed on the computer device on the model of the target area. In an embodiment in which more than two input points are received by the computing device, the computing device calculates a linear measurement as a sum of a first point to a second point and from the second point to a third point (which additional points being calculated in a similar manner).

In addition, in an embodiment, the computing device automatically calculates a perimeter of a target area after receiving a plurality of inputs from a device user or from an automated process executed on the computer device on the model of the target area. Specifically, in an embodiment, the computing device receives a plurality of inputs from a device user or from an automated process executed on the computer device indicating points on the model of the target area that correspond to an outer boundary of the target area. Subsequent to receiving the plurality of inputs from the device user or from an automated process executed on the computer device, the computing device automatically calculates the perimeter of the target area as a sum of the Euclidean distances between every two subsequent points of the plurality inputs corresponding to outer boundaries of the target area.

Moreover, in an embodiment, after receiving the input of a perimeter approximation from a device user or from an automated process executed on the computing device, the computing device automatically calculates each dimension that is related to or derived from the perimeter, including the length, width, depth, surface area, and volume. For example, in an embodiment, after automatically calculating the perimeter of the target area, the computing device automatically calculates a surface area of the target area. Specifically, based on the calculated perimeter of the target area, the computing device automatically overlays a plurality of mesh triangles within the perimeter of the model of the target area as defined by the boundaries previously received by the computing device. After overlaying the plurality of mesh triangles within the perimeter of the model of the target area, the computing device automatically calculates a sum of the area of each of the plurality of mesh triangles, thereby automatically calculating the surface area of the target area. In an embodiment, the computing device can receive an instruction to add or to remove one or more mesh triangles from the plurality of mesh triangles to fine tune the calculation of the surface area of the target area.

In addition, in an embodiment, the computing device automatically calculates the perimeter approximation using an image segmentation process on 2D images to identify a contour of the skin anomaly, with the 2D images being input into a photogrammetry model to output a generated 3D model of the interior of the skin anomaly. As such, the perimeter can be extracted from the generated 3D model, and the computing device can automatically calculate each dimension that is related to or derived from the perimeter, including the length, width, depth, surface area, and volume.

In an embodiment, a second set of three-dimensional scans of the target area are received by the computing device, with the second set of 3D scans being taken at a point in time that is later than that of a first set of 3D scans. As such, the computing device receives time-spaced 3D scans of substantially the same target area, and the computing device generates models for display to represent a healing timeline of the target area. For example, in some embodiments, models of the target area taken at different times can be simultaneously displaying via the computing device to provide a comparison of the target area across different portions of a healing timeline. The computing device thereby provides for the monitoring and tracking of the target area over time, providing object and consistent data to monitor the evolution of the target area, minimizing individual biases and errors of different health care providers.

Moreover, both for individual sets of 3D scans and for batches of subsequent 3D scans, embodiments of the system facilitate the accurate appraisal, evaluation, and monitoring of, in particular, a perimeter, a surface area, and a depth of the target area. While lengths and widths are more easily measured in two dimensions and using simple distance measurements, perimeters, surface areas, volumes, and depths are typically irregular in dimensions and in resulting calculations; moreover, invasive and uncomfortable contact is typically required to accurately measure a depth of a target area. As such, while perimeters, surface areas, and depths tend to be underestimated or overestimated using simple distance calculations, the system and method provide for the accurate and automated calculations of perimeters, surface areas, volumes, and depths without requiring contact with a subject. Since such complex measurements of perimeters, surface areas, and depths provide more detailed insight into target area healing and progress, the accurate modeling, calculation, and future prediction of such metrics presents an improvement over contact-based and/or linear measurement-based measurements.

In addition, by modeling and displaying representations of the target area in three dimensions and based on 3D scans of the target area, in an embodiment, the system and method provide for interactions with the target area that would typically require contact with the subject. For example, the computing device provides for rotation of the target area model; alterations of the view angle to display different angles and at different heights (such as by zooming in and zooming out); and the use of (or removal of) lighting to provide further insight into the target area. Moreover, in an embodiment, the display device associated with the computing device includes virtual reality, augmented reality, or mixed reality component to provide for the visualization of the target area in a three-dimensional space.

Moreover, in some embodiments, different coloration and/or thermal information is displayable via the computing device for the 3D scans, with the color and thermal information being storable within the computing device and associated with the target area across different stages of healing. Together with the 3D scans and the automated calculations described in detail above, the data received by, generated by, and generated via the computing device can be documented and stored on the computing device associated with the target area and the subject. Moreover, in an embodiment, the data received by, generated by, and generated via the computing device can be integrated into or otherwise associated with an electronic health record associated with the subject.

In an embodiment of the system and method, via the computing device, target area tracking includes an output of a healing progress prediction based on previously received 3D scans of the target area. Specifically, in an embodiment, the system and method include an automatic calculation of predicted target area characteristics (such as length, width, depth, perimeter, surface area, and volume) based on previously received and calculated characteristics. Moreover, some embodiments of the system and method include the display of the predicted target area including the predicted target area characteristics. As such, embodiments of the system provide for the simulation and prediction of healing progress for a target area. In some embodiments, machine learning and other artificial intelligence-based feedback systems are used to enhance predicted target area characteristics based on the success or failure of previous predictions.

Experimental Results

A pilot study was conducted to compare measurements taken by a physical measurement, a two-dimensional (2D) image measurement, and a three-dimensional (3D) image measurement in accordance with the system and method described in greater detail above. Each measurement was compared to a control measurement performed via a digital caliper having a resolution of 0.01 mm. The resolution of the wound images was 250×250 pixels. Based on the pixel dimensions of wound images, the resolution of the image measurements was 0.48 mm. The mesh resolution (the distance between the vertices of the mesh, which determines the resolution of measurements made via the system and method) of the 3D images was 0.5 mm.

For the physical measurements, four simulated wounds were disposed on a surface, and measurements were made by participants via the digital caliper (for length and width) and via a cotton swab (for depth). For the 2D measurements, color images of the simulated wounds were taken from a top-down view (for length, width, perimeter, and surface area) and three images taken from different angles (for depth), with the 2D images printed onto a piece of paper. For the 3D measurements, color scans of the simulated wounds were displayed on a display device in communication with a computing device.

Participants were asked to measure the length, width, depth, perimeter, and surface area of the four simulated wounds using each of the physical, 2D image, and 3D scan techniques. To measure the length, width, and depth on the physical and 2D image sets, participants used the digital caliper to take measurements. To measure the perimeter and surface area on the physical and 2D image sets, participants calculated the measurements using any suitable measurement estimation as determined by each participant. To measure the length, width, depth, perimeter, and surface area on the 3D scan dataset, participants input start points and end points via the system and method described in greater detail above.

Based on the data measurements received from the participants, the inter-rater reliability of the measurement techniques was analyzed. The inter-rater reliability was used to measure agreement between raters, with high agreement between raters indicating that the measurement technique produces consistent results and is reliable. Two-way mixed intraclass correlation coefficient (ICC) values were used to analyze the inter-rater reliability (with results shown in Table 1 below).

TABLE 1

Inter-rater reliability of measurement techniques analyzed as ICC values. All comparisons have a p-value of <.001

| | Intraclass correlation coefficient (ICC) values | | |
|---|---|---|---|
| Measurement | Physical | Image | System and Method |
| Length | 0.996 | 0.998 | 0.999 |
| Width | 0.987 | 0.995 | 0.975 |
| Depth | 0.956 | 0.866 | 0.951 |
| Perimeter | 0.883 | 0.910 | 0.998 |
| Surface Area | 0.861 | 0.918 | 0.999 |

In addition, the variability between the techniques was analyzed by comparing values of length, width, depth, perimeter, and surface area for each wound using the Friedman test and subsequent Conover post hoc tests. The Friedman test is a nonparametric test equivalent to the repeated measures ANOVA test and was used because the data was not normally distributed. Standard error (SE) was calculated as $$\sigma/\sqrt{n},$$

where σ represents the standard deviation (SD) and n represents the number of samples (n=18). The standard deviation was used to evaluate the precision of the techniques. Results from these analyses are shown in Table 2, shown in FIG. 2.

The lowest SD for the length measurements of wounds 2-4 was observed from the system and method described in detail above; for wound 1, the lowest SD for the length was measured from the 2D image technique. Similarly, the lowest SD for the width measurements of wounds 1, 2, and 4 was measured from the system and method described in detail above, with the lowest SD for the width for wound 3 measured from the 2D image technique. The lowest SD for the perimeter and surface area measurements for wounds 1-4 was measured from the system and method described in detail above.

Referring again to Table 1 above, ICC values were greater than 0.8 for length, width, depth, perimeter, and surface area for each of the physical, 2D image, and 3D scan measurement techniques, indicating high reliability of all three techniques for all measurements. ICC values greater than 0.9 were observed for the physical length, width, and depth measurements, but not for perimeter or surface area measurements. Similarly, ICC values greater than 0.9 were observed for the 2D image length, width, perimeter, and surface area measurements, but not for depth measurements. For the 3D scans in accordance with the system and method described in detail above, ICC values greater than 0.9 were observed for all measurements, including length, width, depth, perimeter, and surface area measurements. The lowest ICC values observed were 0.861 for physical surface area, 0.866 for 2D image depth, and 0.883 for physical perimeter.

Statistically significant ($p<0.05$) differences in length measurements were observed between the physical, 2D image, and 3D scan measurement techniques for wounds 1-4. Pair-wise comparisons revealed statistically significant length measurement differences between the physical and 2D image techniques for wounds 2-4; between the physical and 3D scan measurements for wound 1; and between the 2D image and 3D scan techniques for wounds 2 and 4.

In addition, statistically significant differences in width measurements were observed between the physical, 2D image, and 3D scan measurement techniques for wounds 1-4. Pair-wise comparisons revealed statistically significant width measurement differences between the physical and 2D image techniques for wounds 1-4; between the physical and 3D scan measurements for wounds 2-4; and between the 2D image and 3D scan techniques for wounds 2 and 4.

Statistically significant differences in depth measurements were observed between the physical, 2D image, and 3D scan measurement techniques for wounds 3 and 4. Pair-wise comparisons revealed statistically significant width measurement differences between the physical and 2D image techniques for wounds 3 and 4; between the physical and 3D scan measurements for wound 4; and between the 2D image and 3D scan techniques for wound 3.

Moreover, statistically significant differences in perimeter measurements were observed between the physical, 2D image, and 3D scan measurement techniques for wounds 2-4. Pair-wise comparisons revealed statistically significant width measurement differences between the physical and 2D image techniques for wounds 1-4; between the physical and 3D scan measurements for wound 2; and between the 2D image and 3D scan techniques for wound 4.

Finally, statistically significant differences in surface area measurements were observed between the physical, 2D image, and 3D scan measurement techniques for wounds 2-4. Pair-wise comparisons revealed statistically significant width measurement differences between the physical and 2D image techniques for wounds 2 and 4; between the physical and 3D scan measurements for wounds 1-4; and between the 2D image and 3D scan techniques for wounds 3 and 4. Results for each comparison are shown in the Friedman and Conover tests in Table 2 (shown in FIG. 2).

Looking specifically at variability, there were statistically significant differences between the techniques, primarily between the physical and 2D image techniques. Despite the high inter-rater reliability of the physical and 2D image measurement techniques, the high variability indicates that the physical and 2D image techniques are inherently susceptible to error.

Since there is a great deal of variability between measurements, repeatability is an important concern for skin abnormality site management, monitoring, and tracking. Given that physical examinations cannot be repeated under identical conditions, 2D images and 3D scans represent techniques with greater repeatability. However, since 2D images are prone to distortion and warping and do not accurately depict curved surfaced, 3D scans under the system and method described in greater detail above represent topographically accurate views having high repeatability. The consistently excellent ICC values of greater than 0.9 for each measurement performed via the system and method indicates greater overall inter-rater reliability compared to physical and 2D image-based measurements. This is particularly true for the complex measurements of surface area and perimeter (compared to simpler measurements of length, width, and depth), wherein the system and method automatically calculated surface area and perimeter with greater inter-rater reliability than the physical and 2D image-based measurements.

Computer and Software Technology

The present invention may be embodied on various platforms. The following provides an antecedent basis for the information technology that may be utilized to enable the invention.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read-only memory (ROM); random access memory (RAM); magnetic disk storage media; optical storage media; flash memory devices; electrical, optical, acoustical, or other forms of propagated signals (e.g., carrier waves, infrared signals, digital signals, etc.), and others.

Further, firmware, software, routines, instructions may be described herein as performing certain actions. However, it should be appreciated that such descriptions are merely for convenience and that such actions, in fact, result from computing devices, processors, controllers, or other devices executing the firmware, software, routines, instructions, etc.

The machine-readable medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any non-transitory, tangible medium that can contain or store a program for use by or in connection with an instruction execution system, apparatus, or device. Storage and services may be on-premises or remote, such as in the "cloud" through vendors operating under the brands MICROSOFT AZURE, AMAZON WEB SERVICES, RACKSPACE, and KAMATERA.

A machine-readable signal medium may include a propagated data signal with machine-readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a computer-readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk, or the like.

Program code embodied on a machine-readable medium may be transmitted using any appropriate medium, including but not limited to wireless, wireline, optical fiber cable, radiofrequency, etc., or any suitable combination of the foregoing. Machine-readable program code for carrying out operations for aspects of the present invention may be written in any combination of one or more programming languages, including an object-oriented programming language such as Java, C#, C++, Visual Basic, or the like and conventional procedural programming languages, such as the "C" programming language or similar programming languages. Additional languages may include scripting languages such as PYTHON, LUA, and PERL.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by machine-readable program instructions.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A method of skin anomaly assessment, measurement, and monitoring comprising the steps of:

receiving, at a computing device, one or more three-dimensional scans of a skin anomaly defining a three-dimensional topology of the skin anomaly;

converting, via the computing device, the one or more three-dimensional scans into a three-dimensional model of the skin anomaly, the three-dimensional model having characteristics and dimensions matching the three-dimensional topology, wherein the computing device automatically aligns the three-dimensional model using an optimization process to align a mesh of the three-dimensional model with the three-dimensional topology defined by the one or more three-dimensional scans via translation, rotation, and scale;

displaying, via a display device in communication with the computing device, the three-dimensional model;

receiving, on the three-dimensional model and via the computing device, an input of at least a start point and an end point, the start point and the end point associated with at least one dimension of the three-dimensional model of the skin anomaly; and automatically calculating, based on the input of at least the start point and the end point, a dimension of the skin anomaly, the dimension selected from the group consisting of a length, a width, a depth, a perimeter, a surface area, and a volume, wherein the computing device calculates the length, the width, or the depth as a Euclidean distance between the start point and the end point.

2. The method of claim 1, further comprising the step of automatically calculating, based on a plurality of inputs received on the three-dimensional model and via the computing device, each of the length, the width, the depth, the perimeter, the surface area, and the volume of the skin anomaly, wherein the plurality of inputs indicate points on the three-dimensional model corresponding to an outer boundary of the skin anomaly, the perimeter is calculated as a sum of Euclidean distances between every two subsequent points of the plurality of inputs, the surface area is calculated by overlaying a plurality of mesh triangles of the mesh of the three-dimensional model within the perimeter of the three-dimensional model and summing an area of each of the plurality of mesh triangles, and the volume is automatically calculated as a dimension related to or derived from the perimeter.

3. The method of claim 1, wherein the one or more three-dimensional scans are a first set of three-dimensional scans, further comprising the step of receiving, at the computing device, a second set of three-dimensional scans of the skin anomaly, the second set of three-dimensional scans being taken at a point in time later than the first set of three-dimensional scans such that the first set and the second set are time-spaced three-dimensional scans of substantially the same skin anomaly.

4. The method of claim 3, wherein the three-dimensional model of the skin anomaly is a first three-dimensional model of the skin anomaly, further comprising the step of converting, via the computing device, the second set of three-dimensional scans into a second three-dimensional model of the skin anomaly, wherein the computing device automatically aligns the second three-dimensional model using an optimization process to align a mesh of the second three-dimensional model with the three-dimensional topology of the skin anomaly defined by the second set of three-dimensional scans via translation, rotation, and scale.

5. The method of claim 4, further comprising the step of tracking, via the computing device, differences in dimensions between the first three-dimensional model and the second three-dimensional model to represent a healing timeline of the skin anomaly.

6. The method of claim 5, further comprising the step of generating, via the computing device and based on the differences in dimensions between the first three-dimensional model and the second three-dimensional model, a simulated healing model for the skin anomaly, wherein the simulated healing model is based on the surface area and the perimeter of each of the first three-dimensional model and the second three-dimensional model.

7. The method of claim 6, wherein the differences in dimensions between the first three-dimensional model and the second three-dimensional model are selected from the group consisting of the surface area, the perimeter, the length measured along a surface of the skin anomaly, the width measured along the surface of the skin anomaly, and the depth measured along the surface of the skin anomaly.

8. The method of claim 3, further comprising the step of pretraining, from a database of skin anomaly healing progression images, a machine learning model on the computing device.

9. The method of claim 8, further comprising the step of generating, via the computing device and based on the machine learning model, a simulated healing model for the skin anomaly, wherein the simulated healing model is based on the surface area and the perimeter of the three-dimensional model.

10. The method of claim 9, wherein the simulated healing model is based on differences in dimensions that are selected from the group consisting of the surface area, the perimeter, the length measured along a surface of the skin anomaly, the width measured along the surface of the skin anomaly, and the depth measured along the surface of the skin anomaly.

11. The method of claim 10, wherein the three-dimensional model of the skin anomaly is a first three-dimensional model of the skin anomaly, the method further comprising the steps of:

converting, via the computing device, the second set of three-dimensional scans into a second three-dimensional model of the skin anomaly, wherein the computing device automatically aligns the second three-dimensional model using an optimization process to align a mesh of the second three-dimensional model with the three-dimensional topology of the skin anomaly defined by the second set of three-dimensional scans via translation, rotation, and scale;

comparing the second three-dimensional model of the skin anomaly to the simulated healing model for the skin anomaly; and based on a determination that each of the surface area and the perimeter of the second three-dimensional model of the skin anomaly is greater than a surface area and a perimeter of the simulated healing model for the skin anomaly, generating, via the computing device, an alert.

12. The method of claim 1, wherein the display device includes a digital overlay component selected from the group consisting of virtual reality, augmented reality, and mixed reality, such that the three-dimensional model is simultaneously interactable to a plurality of different users via the digital overlay component.

13. The method of claim 12, wherein the step of displaying the three-dimensional model further comprises displaying, via a plurality of display devices that are remote to each other, the three-dimensional model at different locations.

14. The method of claim 1, further comprising the step of integrating the three-dimensional model and the automatically calculated dimension of the skin anomaly into an electronic health record of a subject associated with the skin anomaly.

15. The method of claim 1, further comprising the step of establishing a spatial anchor for the three-dimensional model, wherein the computing device is configured to receive one or more additional measurements from the spatial anchor.

* * * * *